(12) United States Patent
Alberici et al.

(10) Patent No.: US 11,590,305 B2
(45) Date of Patent: Feb. 28, 2023

(54) MANUAL RESUSCITATION BAG WITH IMPROVED PEP EXHAUST VALVE

(71) Applicant: Air Liquide Medical Systems, Antony (FR)

(72) Inventors: Luca Alberici, Roncadelle (IT); Ottorino Bugatti, Sarezzo (IT); Paolo Massaro, Brescia (IT); Fulvio Masserdotti, Nave (IT)

(73) Assignee: Air Liquide Medical Systems, Antony (FR)

( * ) Notice: Subject to any disclaimer, the term of this patent is extended or adjusted under 35 U.S.C. 154(b) by 615 days.

(21) Appl. No.: 16/741,909

(22) Filed: Jan. 14, 2020

(65) Prior Publication Data
US 2020/0222648 A1 Jul. 16, 2020

(30) Foreign Application Priority Data

Jan. 15, 2019 (EP) .................................... 19151951

(51) Int. Cl.
*A61M 16/00* (2006.01)
*A61M 16/10* (2006.01)
(Continued)

(52) U.S. Cl.
CPC .... *A61M 16/0084* (2014.02); *A61M 16/0875* (2013.01); *A61M 16/1005* (2014.02);
(Continued)

(58) Field of Classification Search
CPC ............ A61M 16/0084; A61M 16/201; A61M 16/0078; A61M 16/20; A61M 16/204; A61M 16/205
See application file for complete search history.

(56) References Cited

U.S. PATENT DOCUMENTS

| 5,109,840 A | 5/1992 | Daleiden |
| 5,301,667 A | 4/1994 | McGrail et al. |

(Continued)

FOREIGN PATENT DOCUMENTS

| EP | 0 743 075 | 11/1996 |
| WO | WO 2005 021074 | 3/2005 |

(Continued)

OTHER PUBLICATIONS

European Search Report and Written Opinion for corresponding EP 19151951, dated Jun. 17, 2019.

*Primary Examiner* — Margaret M Luarca
(74) *Attorney, Agent, or Firm* — Allen E. White

(57) ABSTRACT

The invention concerns a manual resuscitation bag having a first PEP exhaust valve (4) arranged in a first conduit element (3) and fluidly communicating with the ambient atmosphere for venting gas to the atmosphere when the gas pressure, into the first conduit element (3), exceeds a given pressure threshold. The first PEP exhaust valve (4) has a valve body (5) and a calibration mechanism (6, 12; 7-10) for setting a desired pressure threshold. The calibration mechanism (6, 12; 7-10) is a rotatable member (6), actuatable by a user, arranged on the valve body (5) and cooperating with a pressure adjusting device (7-10) arranged into the valve body (5), and a support member (12) comprising several markings (11) corresponding to several settable pressure values, arranged between the rotatable member (6) and the valve body (5).

15 Claims, 4 Drawing Sheets

(51) Int. Cl.
*A61M 16/12* (2006.01)
*A61M 16/20* (2006.01)
*A61M 16/08* (2006.01)

(52) U.S. Cl.
CPC ........ *A61M 16/125* (2014.02); *A61M 16/201* (2014.02); *A61M 2202/0208* (2013.01); *A61M 2205/70* (2013.01)

(56) References Cited

U.S. PATENT DOCUMENTS

| | | |
|---|---|---|
| 5,647,354 A | 7/1997 | Lakhani et al. |
| 2004/0007235 A1* | 1/2004 | Rafoss .............. A61M 16/0078 128/207.14 |
| 2012/0012111 A1 | 1/2012 | Howe, Jr. et al. |

FOREIGN PATENT DOCUMENTS

| | | |
|---|---|---|
| WO | WO 2005 035065 | 4/2005 |
| WO | WO 2009 032932 | 3/2009 |
| WO | WO 2015 041396 | 3/2015 |
| WO | WO 2017 096286 | 6/2017 |
| WO | WO 2017 200399 | 11/2017 |
| WO | WO 2019 001751 | 1/2019 |

\* cited by examiner

MANUAL RESUSCITATION BAG WITH IMPROVED PEP EXHAUST VALVE

CROSS REFERENCE TO RELATED APPLICATIONS

This application claims the benefit of priority under 35 U.S.C. § 119 (a) and (b) to European Patent Application No. 19151951, filed Jan. 15, 2019, the entire contents of which are incorporated herein by reference.

BACKGROUND

The present invention relates to a manual artificial respiration device or system, commonly called a manual resuscitation bag or the like, with a PEP exhaust valve that can be used for resuscitating a person, i.e. a patient, in state of cardiac arrest, comprising improved means for easily setting a desired pressure threshold of the PEP exhaust valve.

Cardiac arrest is a condition affecting hundreds of thousand people every year with a very poor prognosis. One of the main life-saving actions is to apply thoracic compressions or 'TCs' along with brief intervals of lung ventilation with a resuscitation bag. TCs are successive compressions and decompressions exerted by a rescuer on the thoracic cage of the person, i.e. the patient, in cardiac arrest. TCs aim at partially restoring inhalation and exhalation phases and therefore gas exchanges in the lungs, as well as promoting or restoring blood circulation in the body and toward the organs, especially in the brain of the patient.

As the compressions and decompressions exerted by the rescuer mobilize only small volumes of gas, in and out of the patient's airways, it is advocated to perform regularly further gas insufflations to bring a fresh $O_2$-containing gas into the lungs, such as air or $O_2$-enriched air, thereby enhancing the gas exchanges.

The flow of respiratory gas delivered to the patient, at a positive pressure, helps keeping the alveoli of the lungs open thereby promoting and/or enhancing gas exchanges. In addition, the positive pressure creates a resistance to gas expulsion during the TC phases, which improves the energy transmission to the heart thereby promoting a better cardiac output.

It is recommended to interpose 2 gas insufflations every 30 chest compressions, whereas the ideal rate of compressions is of between 100 and 120 compressions per minute (c/min).

Usually, the flow of respiratory gas is delivered by an manual resuscitation bag, also called "resuscitation bag system", "resuscitation bag device" or similar, that is fluidly connected to ambient air and, if need be, to an oxygen source.

A manual resuscitation bag generally comprises a deformable bag on which a rescuer can exert a manual-pressure, i.e. he/she can manually squeeze it, for sending the respiratory gas to the patient. The respiratory gas flowing out of the deformable bag is subsequently delivered to the patient's airways, by means of a respiratory interface, such as a facial mask, a laryngeal mask, an endotracheal tube or the like.

Examples of such manual resuscitation bags are given by documents WO-A-2017/096286, WO2015/041396, WO2005/035065 and EP-A-0743075.

For avoiding overpressures in the manual resuscitation bag, in particular overpressures in the conduit element fluidly connected to the gas inlet of the deformable bag, it has been proposed to arrange upstream of the deformable bag of the manual resuscitation bag, namely in said conduit element fluidly connected to the gas inlet, a PEP exhaust valve that is in fluid communication with the ambient atmosphere for venting gas, i.e. gaseous overpressures, to the atmosphere when the gas pressure exceeds a given pressure threshold into said conduit element.

However, a problem is that setting a desired pressure threshold can be difficult for the rescuer, while the manual resuscitation bag is used, i.e. while compressions and decompressions are provided by the rescuer to the patient in cardiac arrest, as existing PEP exhaust valves comprise side or lateral pressure markings carried by the peripheral surface of the valve body. Such a lateral or side positioning of the pressure markings is not convenient as it obligates the rescuer to tilt his head for reading the markings and setting the desired pressure, which is neither comfortable nor convenient, and further may result in parallax issues leading to wrong pressure settings.

SUMMARY

A main goal of the present invention is to fix the problem encountered with current manual resuscitation bags, in particular to provide an improved manual resuscitation bag allowing a convenient, quick and safe setting of the PEP pressure threshold value.

A solution according to the present invention concerns a manual resuscitation bag comprising:
- a deformable bag comprising a gas inlet and a gas outlet,
- a first conduit element fluidly connected to the gas inlet of the deformable bag, and
- a first PEP exhaust valve arranged in the first conduit element and fluidly communicating with the ambient atmosphere for venting gas to the atmosphere when the gas pressure, into the first conduit element, exceeds a given pressure threshold, said first PEP exhaust valve comprising a valve body and means for setting a desired pressure threshold, characterized in that the means for setting the pressure threshold comprise:
- a rotatable member, actuatable by a user, arranged on the valve body and cooperating with pressure adjusting means arranged into the valve body, and
- a support member comprising several markings corresponding to several settable pressure values, arranged between the rotatable member and the valve body, and wherein the rotatable member further comprises a reading window that can be positioned so as to face one of the markings, when the user actuates the rotatable member, thereby selecting a pressure threshold corresponding to one of the pressure values indicated by the markings that is readable through said reading window.

Depending on the embodiment, a manual resuscitation bag according to the present invention can comprise of one or several of the following additional features:
- the first PEP exhaust valve comprises an axis (A-A).
- the support member comprising the markings is a disk shape.
- only one (i.e. a unique) marking is readable through the reading window.
- the support member is fixed with respect to the valve body.
- the rotatable member is mobile in rotation with respect to the valve body and to the disk member.
- the support member is secured to or made integral with the valve body.

the support member comprises an annular part, a central orifice and at least one fixation leg projecting away from the annular part, preferably at least two fixation legs or more.

the valve body comprises an central passage and at least one axially-arranged groove, said at least one axially-arranged groove lodging at least one fixation leg of the support member, when the support member is positioned on and secured to the valve body.

the valve body comprises at least two axially-arranged grooves cooperating with at least two fixation legs of the support member.

the support member comprises an upper (i.e. outer) surface carrying the markings.

the rotatable member comprises a top wall and an annular body projecting from said top wall, i.e. it has a cup-like shape.

the annular body of the rotatable member forms a sleeve around (at least a part of) the valve body.

the reading window is arranged in the top wall of the rotatable member, i.e. the reading window traverses the top wall.

the rotatable member further comprises an inner axially-projecting bulb cooperating with the pressure adjusting means arranged into the valve body.

the pressure adjusting means arranged into the valve body comprise a piston head, a spring element and a valve seat cooperating with the piston head for adjusting the pressure threshold.

the piston head is secured to a piston rod, i.e. carried by the piston rod.

the spring element is arranged around at least a portion of the piston rod.

the rotatable member is screwed on the valve body.

the inner axially-projecting bulb of the rotatable member traverses the central orifice of the support member.

the inner axially-projecting bulb of the rotatable member has a tubular shape, preferably a cylindrical or tronco-conical shape.

the inner axially-projecting bulb of the rotatable member allows the piston rod to be positioned correctly thereby allowing the piston head to work properly.

the piston rod is secured to the inner axially-projecting bulb.

the valve body, the rotatable member and the support member are co-axially arranged, i.e. on axis (A-A).

the support member comprises markings corresponding to several pressure values comprising 0, 5 and 10 cmH$_2$O.

the manual resuscitation bag further comprises a gas reservoir comprising an outlet orifice, the first conduit element being fluidly connected to the outlet orifice of the gas reservoir.

a first one-way admission valve is arranged in the first conduit element and fluidly communicating with the ambient atmosphere for allowing ambient air to enter into the first conduit element.

a second one-way valve is arranged in the first conduit element between the first one-way admission valve and the gas inlet of the deformable bag for allowing the gas to travel only from the first conduit element to the deformable bag.

the opening pressure of PEP exhaust valve is of between 0 cm H$_2$O and 30 cm H$_2$O, preferably of between 0 cm H$_2$O and 15 cm H$_2$O.

the first conduit element comprises an oxygen entry arranged between the outlet orifice of the gas reservoir and the second one-way valve.

the first conduit element comprises a inner passage or lumen for the gas.

the valve body of the first PEP exhaust valve is in fluid communication with the lumen of the first conduit.

the manual resuscitation bag comprises a gas conduit in fluid communication with the gas outlet of the deformable bag.

the manual resuscitation bag further comprises an overpressure valve arranged in the gas conduit in fluid communication with the gas outlet of the deformable bag.

the manual resuscitation bag further comprises a third one-way valve arranged in the gas conduit downstream of the overpressure valve.

the manual resuscitation bag further comprises further a pneumatic control valve arranged in the gas conduit downstream of the third one-way valve.

the manual resuscitation bag further comprises a gas delivery conduit in fluid communication with the gas conduit for conveying at least part of the gas circulating into the gas conduit to a patient interface.

the patient interface comprises of a respiratory mask or a tracheal cannula.

the gas conduit conveys at least a part of the gas exiting the deformable bag through the gas outlet.

the overpressure valve is configured to vent to the atmosphere at least part of the gas present in the gas conduit, when the gas pressure in the gas conduit exceeds a given value.

the manual resuscitation bag further comprises of a second one-way valve arranged in a conduit in fluid communication with the gas inlet of the deformable bag.

a third one-way valve is arranged in the gas conduit and configured for allowing a circulation of gas in the gas conduit only in the direction from the deformable bag toward the pneumatic valve.

BRIEF DESCRIPTION OF THE DRAWINGS

Preferred embodiments according to the present invention are shown in the enclosed Figures, among which.

DETAILED DESCRIPTION OF THE PREFERRED EMBODIMENTS

Figure 1:
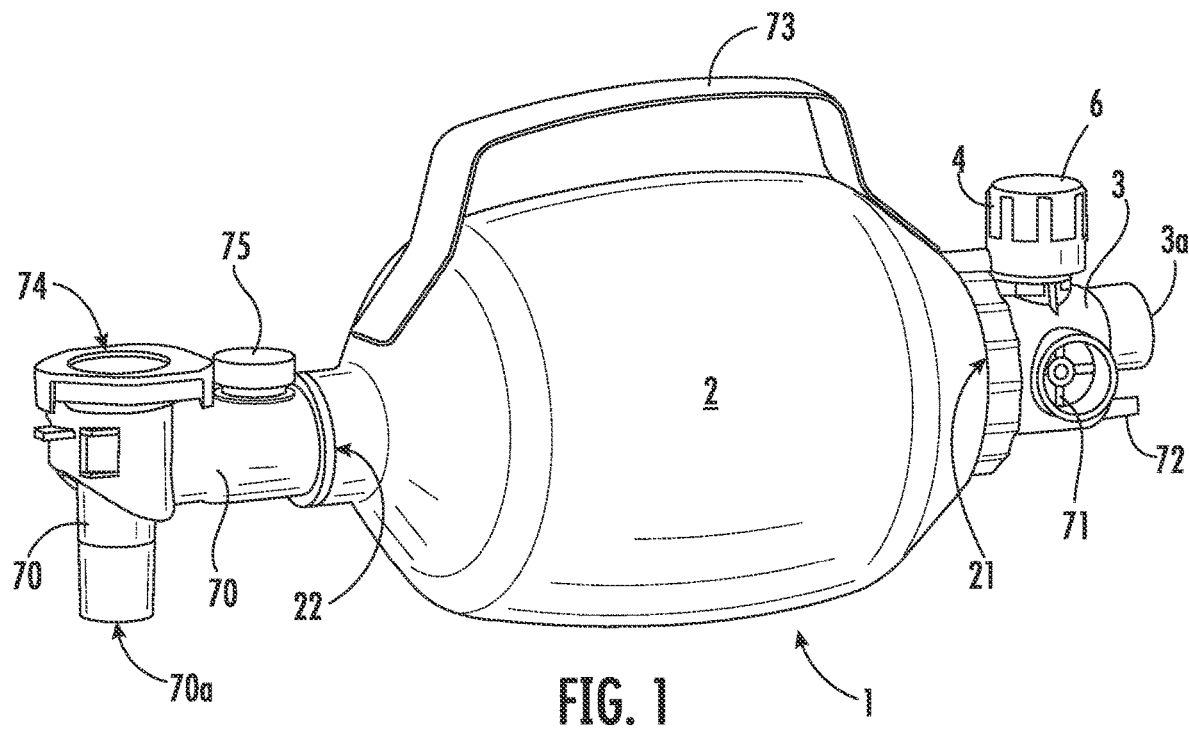
FIG. 1 represents a side view of an embodiment of a manual resuscitation bag according to the present invention.
Figure 2:
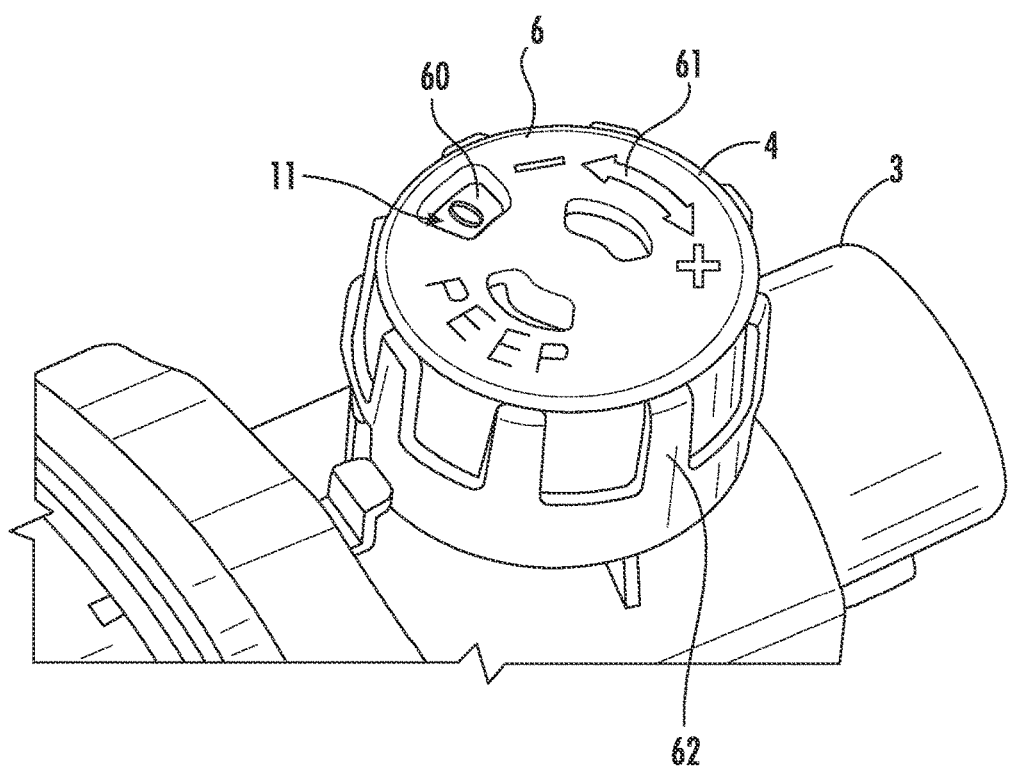
FIG. 2 is an enlarged view of the PEP valve of the resuscitation bag of FIG. 1.

FIG. 1 is a side view of an embodiment of a manual resuscitation bag 1 according to the present invention comprising a deformable bag 2 having a gas inlet 21 and a gas outlet 22, and a first conduit element 3 fluidly connected to the gas inlet 21 of the deformable bag 2 so as to provide gas, such as air or O$_2$-enriched air, to the deformable bag 2.

The deformable bag 2 is made from a flexible material, such as a polymer. During use, the rescuer manually squeezes the deformable bag 2 for providing gas to the patient.

The first conduit element 3 comprises a conduit entry 3a for connecting a flexible gas reservoir thereto (not shown). In other words, the first conduit element 3 is located between the flexible gas reservoir and the deformable bag 2 so that respiratory gas can travel from the flexible gas reservoir to the deformable bag 2, via the lumen of the first conduit element 3.

The gas outlet 22 of the deformable bag 2 is further in fluid communication with a second conduit element 70 comprising a conduit end 70a, for connecting a respiratory interface thereto (not shown). Typically, the respiratory interface is a respiratory mask, a tracheal cannula or the like, that is designed for feeding the respiratory gas to a patient in cardiac arrest. Advantageously, the manual resuscitation bag 1 comprises also a handle 73 or the like for transporting it.

Further, a first PEP exhaust valve 4 is arranged in the first conduit element 3 and is fluidly communicating with the ambient atmosphere for venting gas, i.e. gas overpressure, to the atmosphere when the gas pressure, into said first conduit element 3, i.e. in its lumen, exceeds a given pressure threshold.

The first PEP exhaust valve 4 comprises a rotatable member 6, such as a rotating knob or the like, a valve body 5 and means for setting a desired pressure threshold including pressure adjusting means arranged into the valve body 5. Said pressure adjusting means 7-11 comprise a piston head 8, a spring element 9, such as a cylindrical spring, and a valve seat 10 cooperating with the piston head 8 for adjusting the pressure threshold. Preferably, the piston head 8 is carried by a piston rod 7 and the spring element 9 is arranged, as a sleeve, around the piston rod 7, typically an elongated rod or the like.

As shown in FIGS. 1, 2, 5 and 6, the rotatable member 6, that is actuatable by a user, namely a rescuer, is arranged on the valve body 5 and cooperates with the pressure adjusting means 7-11 arranged into the valve body 5 for setting a desired overpressure threshold value.

A support member 12 comprising several markings 11 corresponding to several settable pressure values, typically overpressure values of between 0 and 20 cm $H_2O$, is sandwiched between the rotatable member 6 and the valve body 5. Preferably, the support member 12 is secured to the valve body 5 as explained below.

Furthermore, the rotatable member 6 comprises a reading window 60 that can be positioned so as to face one of the markings 11, i.e. the different pressure values. When the user actuates the rotatable member 6, i.e. turns it (see arcuated arrow 61 in FIG. 2) either clockwise (direction "+" in FIG. 2) or counter-clockwise (direction "−" in FIG. 2), a selection of a pressure threshold corresponding to one of the pressure values indicated by the markings 11 is made. The set pressure value is readable through said reading window 60, preferably only one pressure value is visible through the window 60.

Figure 5:
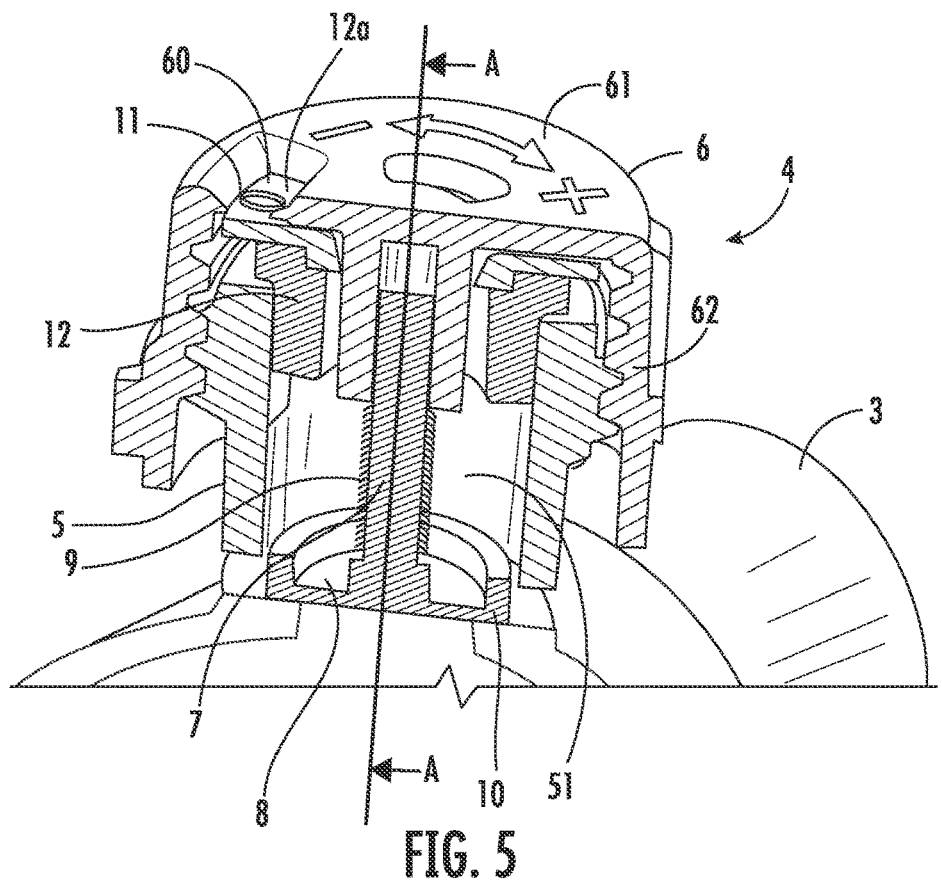
FIG. 5 is a cross-sectional view of the PEP valve of FIG. 2.
Figure 6:
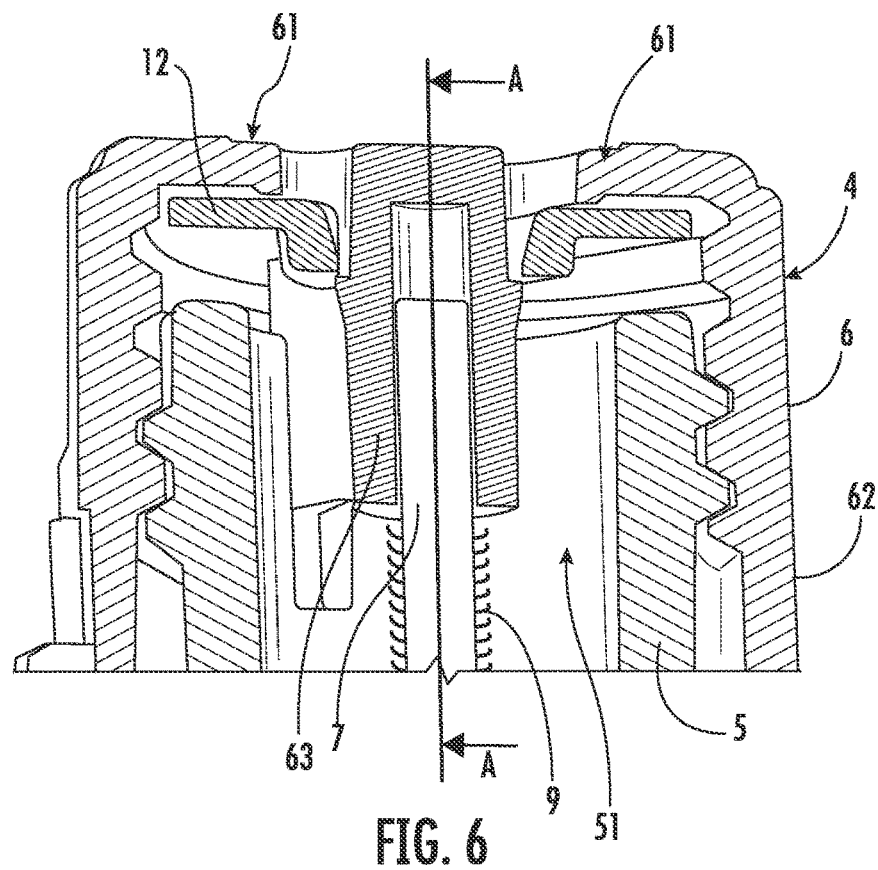
FIG. 6 is a cross-sectional view of the PEP valve of FIG. 2.

As one can see in FIGS. 5 and 6, the valve body 5, the rotatable member 6 and the support member 12 are coaxially arranged on the axis A-A, namely the rotation axis of the rotatable member 6.

The support member 12 can be made from plastic material.

Figure 3:
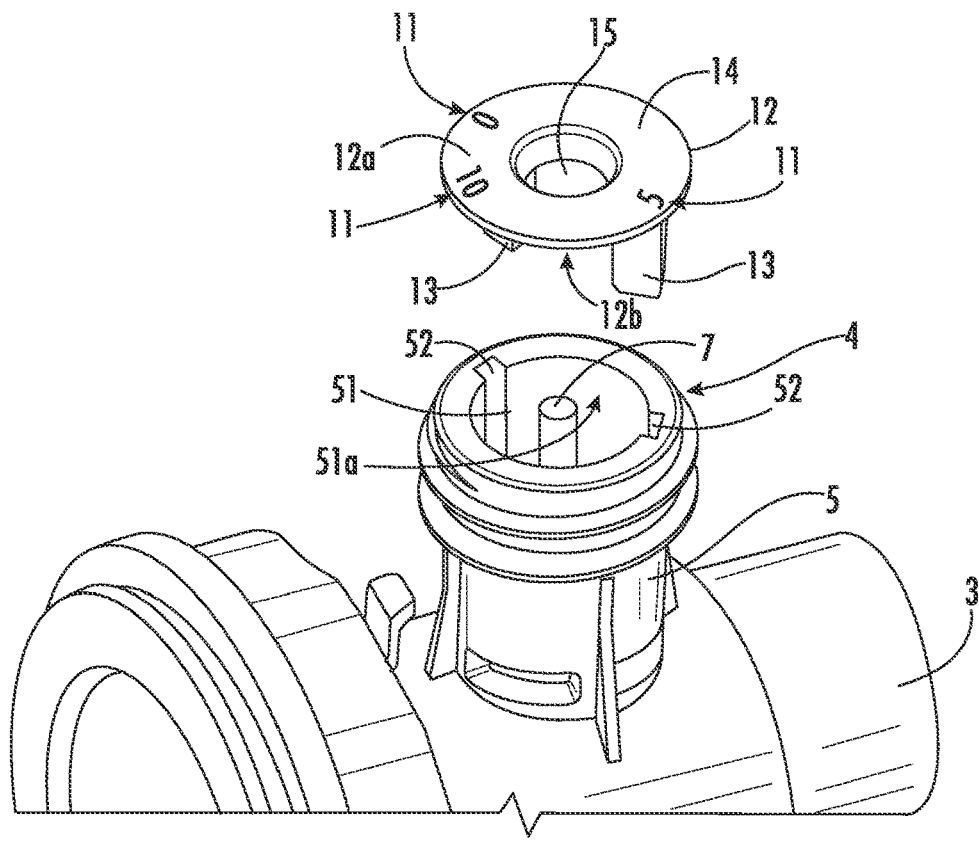
FIG. 3 shows the valve body and the support member of the PEP valve of FIG. 2.
Figure 4:
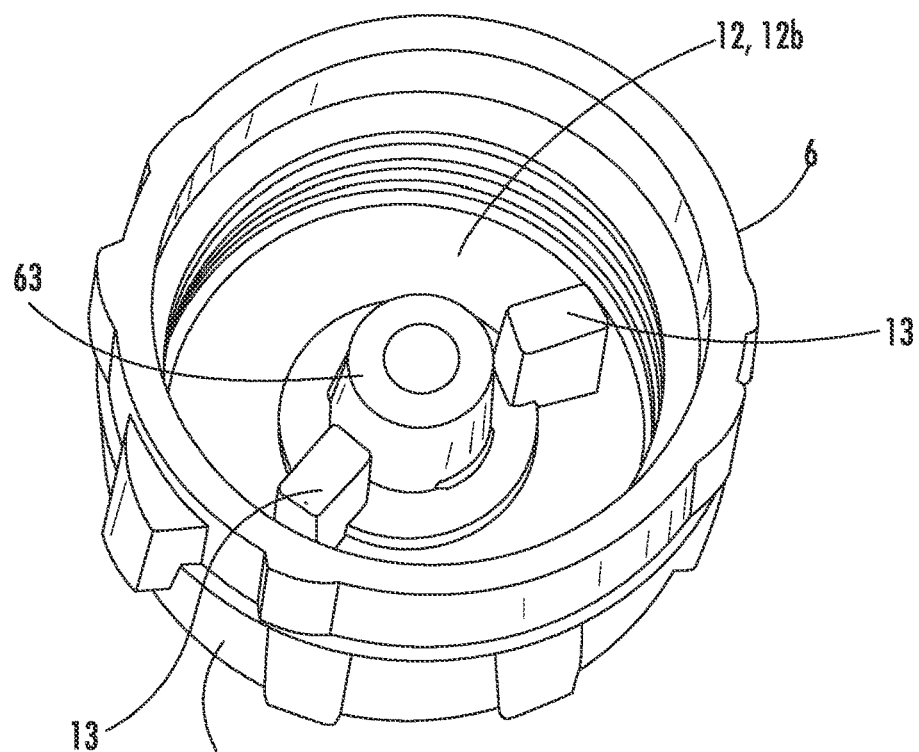
FIG. 4 is an inner view of the rotatable member and the support element of the PEP valve of FIG. 2.

In the embodiment shown in FIGS. 3 and 4, the support member 12 has a disk shape 12. More precisely, it comprises an annular part 14 traversed by a central orifice 15. The markings 11 are carried by the upper surface 12a of the annular part 14 of the support member 12. For instance, the markings 11 can be several pressure values comprising 0, 5 and 10 $cmH_2O$. The markings 11 can be engraved, printed or the like on the upper surface 12a of the annular part 14 of the support member 12.

The annular part 14 further comprises one or more fixation legs 13, preferably at least two fixation legs 13, projecting away from the annular part 14 as shown in FIGS. 3 and 4. As one can see, the two fixation legs 13 are, in the present embodiment, arranged on the rear surface 12b of the annular part 14 of the support member 12. Preferably, they are parallel and project perpendicularly with respect to the rear surface 12b of the support member 12. Those fixation legs 13 are used for securing the support member 12 to the valve body 5.

To this end, the valve body 5 comprises a central passage 51 and one or several axially-arranged groove(s) 52 arranged in the inner wall 51a of the central passage 51 as shown in FIG. 3. Preferably, the number of groves 52 equals the number of fixation legs 13. When the support member 12 is positioned on the valve body 5, the fixation legs 13 of the support member 12 are lodged, i.e. inserted, into corresponding axially-arranged grooves 52 for securing the support member 12 so that it is fixed with respect to the valve body 5.

The rotatable member 6 is then positioned above the valve body 5 and the support member 12 so that said support member 12 is sandwiched between said rotatable member 6 and valve body 5, as shown in FIG. 4 that shows the support member 12 positioned into the rotatable member 6. For instance, the rotatable member 6 can be screwed on the valve body 5.

When positioned and secured to the valve body 5, the annular body 62 of the rotatable member 6 forms a sleeve around the valve body 5. The rotatable member 6 is kept mobile in rotation with respect to the valve body 5 and to the disk member 12, whereas the support member 12 is secured to or made integral with the valve body 5 so as to not move with respect to said valve body 5.

More precisely, as represented in FIGS. 4-7, the rotatable member 6 comprises a top wall 61 and an annular body 62 projecting from said top wall 61, said an annular body 62 forming the sleeve that is positioned around the valve body 5. In other words, the rotatable member 6 has a cup-like shape. The reading window 60 is arranged in the top wall 61, or "roof", of the rotatable member 6.

The rotatable member 6 can be made from plastic material.

Figure 7:
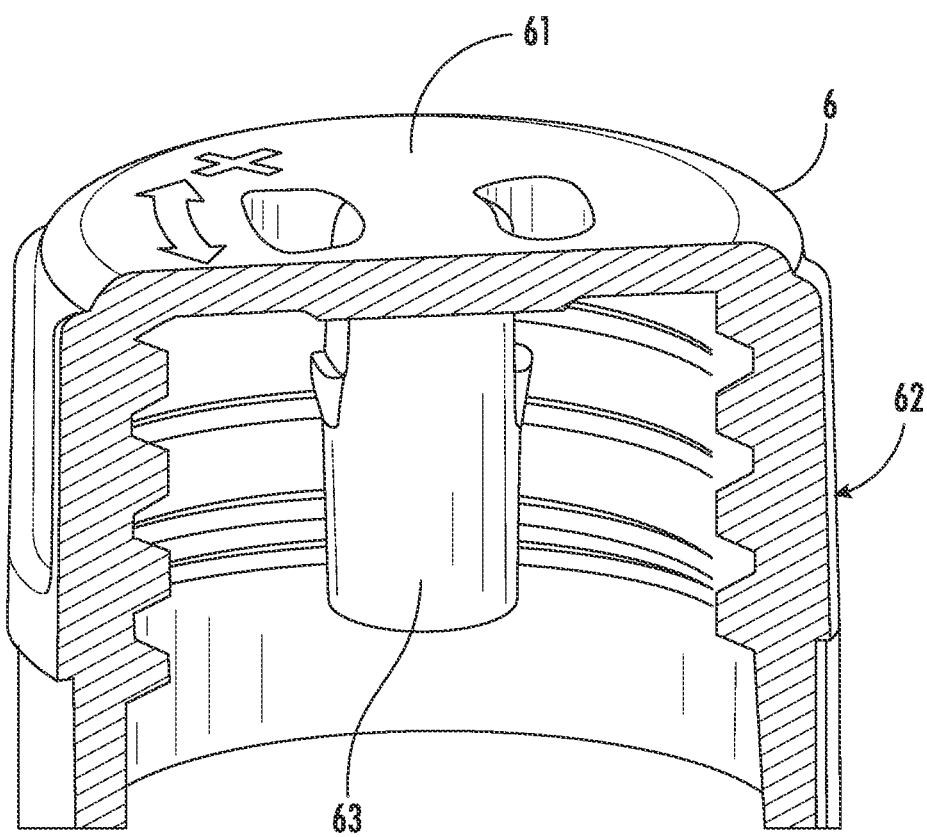
FIG. 7 is a cross-sectional view of the rotatable member of the PEP valve of FIG. 2.

As shown in FIG. 7, the rotatable member 6 further comprises an inner axially-projecting bulb 63, arranged in the center of the rotatable member 6, which cooperates with the pressure adjusting means 7, 8, 9, 10 arranged into the valve body 5. Said pressure adjusting means 7, 8, 9, 10 comprise a piston head 8, a spring element 9 and a valve seat 10 cooperating with the piston head 8 for adjusting the pressure threshold, preferably the piston head 8 is secured to a piston rod 7 and the spring element 9 is arranged around at least a portion of the piston rod 7.

As visible in FIG. 5-6, the inner axially-projecting bulb 63 of the rotatable member 6 traverses the central orifice 15 of the support member 12, when the rotatable member 6 is positioned on the valve body 5. The inner axially-projecting bulb 63 is further secured to the piston rod 7 so as to move upwardly or downwardly said piston rod 7 when the user turns, i.e. rotates, the rotatable member 6, thereby setting the desired pressure level. Indeed, as the piston rod 7 is fixed to the piston head 8, a motion of the piston rod 7 involves a corresponding motion of the piston head 8 that moves more or less away from the valve seat 10, which results in a pressure setting.

Further, the manual resuscitation bag 1 according to the invention can also comprise additional elements or features. For instance, it can comprise also comprise:

an air admission valve 71 in fluid communication with the ambient atmosphere. Air admission valve 71 is preferably arranged on first conduit element 3, as shown in FIG. 1.

a source of an oxygen-containing gas, such as or including a gas cylinder containing oxygen, which is delivered during insufflation phases. Such source of an oxygen-containing gas can be fluidly connected, via an oxygen line, such as a gas conduct, to an oxygen port 72 in fluid communication with the first conduit element 3, as shown in FIG. 1. In this case, the flexible bag 2 can be filled with a mixture of oxygen provided by said oxygen line and ambient air provided by the air admission valve 71 in fluid communication with the ambient atmosphere.

a valve element 74 arranged downstream of the flexible bag 2, for diverting the gas in and out of the patient, during insufflation and exsufflation phases.

an additional exhaust valve arranged in the second conduit 70, i.e. downstream of flexible bag 2.

a pressure relief valve with a lock system 75 arranged downstream of flexible bag 2 for limiting the pressure level, especially during insufflation phases, when the therapy requires a pressure limitation or control.

The manual resuscitation bag of the present invention that comprises the PEP exhaust valve and means for easily setting the pressure threshold of said PEP exhaust valve is suitable for resuscitating a person in state of cardiac arrest or the like.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A manual resuscitation bag (1) comprising:
a deformable bag (2) comprising a gas inlet (21) and a gas outlet (22),
a first conduit element (3) fluidly connected to the gas inlet (21) of the deformable bag (2), and
a first PEP exhaust valve (4) arranged in the first conduit element (3) and fluidly communicating with the ambient atmosphere, the first PEP exhaust valve (4) configured for venting gas to the atmosphere when the gas pressure, into the first conduit element (3), exceeds a given pressure threshold, said first PEP exhaust valve (4) comprising a valve body (5) and a calibration mechanism (6, 12; 7-10) for setting a desired pressure threshold,
characterized in that the calibration mechanism (6, 12; 7-10) for setting the pressure threshold comprises:
a rotatable member (6), actuatable by a user, arranged on the valve body (5) and cooperating with a pressure adjusting device (7-10) arranged into the valve body (5), and
a support member (12) comprising several markings (11) corresponding to several settable pressure values, arranged between the rotatable member (6) and the valve body (5),
and wherein the rotatable member (6) further comprises a reading window (60) that can be positioned so as to face one of the markings (11), when the user actuates the rotatable member (6), thereby selecting a pressure threshold corresponding to one of the pressure values indicated by the markings (11) that is readable through said reading window (60).

2. The manual resuscitation bag according to claim 1, characterized in that the support member (12) comprising the markings (11) is a disk shape (12).

3. The manual resuscitation bag according to claim 1, characterized in that the support member (12) is fixed with respect to the valve body (5), and the rotatable member (6) is mobile in rotation with respect to the valve body (5) and to the support member (12).

4. The manual resuscitation bag according to claim 1, characterized in that the support member (12) comprises an annular part (14), a central orifice (15) and at least one fixation leg (13) projecting away from the annular part (14), preferably at least two fixation legs (13).

5. The manual resuscitation bag according to claim 1, characterized in that the valve body (5) comprises a central passage (51) and at least one axially-arranged groove (52), said at least one axially-arranged groove (52) lodging at least one fixation leg (13) of the support member (12), when the support member (12) is positioned on and secured to the valve body (5).

6. The manual resuscitation bag according to claim 1, characterized in that the support member (12) comprises an upper surface (12*a*) carrying the markings (11).

7. The manual resuscitation bag according to claim 1, characterized in that the rotatable member (6) comprises a top wall (61) and an annular body (62) projecting from said top wall (61).

8. The manual resuscitation bag according to claim 7, characterized in that the annular body (62) of the rotatable member (6) forms a sleeve around the valve body (5).

9. The manual resuscitation bag according to claim 7, characterized in that the reading window (60) is arranged in the top wall (61) of the rotatable member (6).

10. The manual resuscitation bag according to claim 1, characterized in that the rotatable member (6) further comprises an inner axially-projecting bulb (63) cooperating with the pressure adjusting device (7-10) arranged into the valve body (5).

11. The manual resuscitation bag according to claim 10, characterized in that the inner axially-projecting bulb (63) of the rotatable member (6) traverses the central orifice (15) of the support member (12), and the piston rod (7) is secured to the inner axially-projecting bulb (63).

12. The manual resuscitation bag according to claim 1, characterized in that the pressure adjusting device (7-10) arranged into the valve body (5) comprises a piston head (8), a spring element (9) and a valve seat (10) cooperating with the piston head (8) adapted for adjusting the pressure threshold.

13. The manual resuscitation bag according to claim 1, characterized in that the valve body (5), the rotatable member (6) and the support member (12) are co-axially arranged (axis A-A).

14. The manual resuscitation bag according to claim 1, characterized in that the support member (12) comprises markings (11) corresponding to several pressure values comprising 0.5 and 10 cmH$_2$O.

15. The manual resuscitation bag according to claim 1, further comprising:
- a gas reservoir in fluid communication with the first conduit element (3),
- a first one-way admission valve (71) arranged in the first conduit element (3) and fluidly communicating with the ambient atmosphere adapted for allowing ambient air to enter into the first conduit element (3),
- a second one-way valve arranged into the first conduit element (3) between the first one-way admission valve (71) and the gas inlet (21) of the deformable bag (2) adapted for allowing gas to travel only from the first conduit element (3) to the deformable bag (2), and/or
- an oxygen entry (72) in fluid communication with the first conduit element (3) for connecting an oxygen source thereto.

\* \* \* \* \*